(12) United States Patent
Stokes et al.

(10) Patent No.: US 10,675,042 B2
(45) Date of Patent: Jun. 9, 2020

(54) SURGICAL CLIP APPLIER WITH LIVING HINGE JAWS

(71) Applicant: Ethicon LLC, Guaynabo, PR (US)

(72) Inventors: Michael J. Stokes, Cincinnati, OH (US); Gregory Scott, Cincinnati, OH (US); Disha Labhasetwar, Cincinnati, OH (US); John Brady, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 149 days.

(21) Appl. No.: 15/891,581

(22) Filed: Feb. 8, 2018

(65) Prior Publication Data

US 2019/0239889 A1 Aug. 8, 2019

(51) Int. Cl.
| | |
|---|---|
| *A61B 17/128* | (2006.01) |
| *A61B 34/00* | (2016.01) |
| *A61B 34/30* | (2016.01) |
| *A61B 17/29* | (2006.01) |
| *A61B 17/10* | (2006.01) |

(Continued)

(52) U.S. Cl.
CPC ........ *A61B 17/1285* (2013.01); *A61B 17/122* (2013.01); *A61B 34/25* (2016.02); *A61B 34/30* (2016.02); *A61B 34/37* (2016.02); *A61B 17/10* (2013.01); *A61B 34/70* (2016.02); *A61B 90/90* (2016.02); *A61B 2017/00199* (2013.01); *A61B 2017/00477* (2013.01); *A61B 2017/2926* (2013.01); *A61B 2017/2937* (2013.01); *A61B 2017/2939* (2013.01); *A61B 2034/302* (2016.02); *A61B 2034/305* (2016.02); *A61B 2090/0807* (2016.02)

(58) Field of Classification Search
CPC ................ A61B 17/1606; A61B 10/06; A61B 2017/1125; A61B 2018/0225
See application file for complete search history.

(56) References Cited

U.S. PATENT DOCUMENTS

| | | | |
|---|---|---|---|
| 5,171,247 | A | 12/1992 | Hughett |
| 8,403,945 | B2 | 3/2013 | Whitfield et al. |

(Continued)

FOREIGN PATENT DOCUMENTS

| | | |
|---|---|---|
| EP | 2412318 A2 | 2/2012 |
| EP | 2606835 A2 | 6/2013 |
| WO | 2008118928 A2 | 10/2008 |

OTHER PUBLICATIONS

International Search Report and Written Opinion received in corresponding PCT application No. PCT/IB2019/000091 dated Jul. 3, 2019.

*Primary Examiner* — Elizabeth Houston
*Assistant Examiner* — Alyssa M Keane
(74) *Attorney, Agent, or Firm* — Vorys, Sater, Seymour and Pease LLP

(57) ABSTRACT

A surgical clip applier includes a drive housing, an elongate shaft that extends from the drive housing, and an end effector operatively coupled to a distal end of the elongate shaft. The end effector includes jaws that comprise a one-piece body having opposed first and second jaw members. The first jaw member provides a first inner surface and the second jaw member provides a second inner surface opposite the first inner surface. The first and second inner surfaces remain parallel to each other as the first and second jaw members move from an open position to a closed position.

17 Claims, 13 Drawing Sheets

(51) Int. Cl.
*A61B 17/00* (2006.01)
*A61B 17/122* (2006.01)
*A61B 34/37* (2016.01)
*A61B 90/90* (2016.01)
*A61B 90/00* (2016.01)

(56) References Cited

U.S. PATENT DOCUMENTS

| | | |
|---|---|---|
| 9,232,979 B2 | 1/2016 | Parihar et al. |
| 2006/0235437 A1* | 10/2006 | Vitali .................... A61B 17/10 606/142 |
| 2011/0224696 A1 | 9/2011 | Huitema et al. |
| 2015/0351771 A1* | 12/2015 | Malkowski ........ A61B 17/1285 606/143 |
| 2016/0287252 A1 | 10/2016 | Parihar |
| 2016/0296236 A1* | 10/2016 | Whitfield ........... A61B 17/1285 |
| 2018/0036007 A1* | 2/2018 | Fago ................... A61B 17/122 |

* cited by examiner

SURGICAL CLIP APPLIER WITH LIVING HINGE JAWS

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar (i.e., a trocar cannula), a variety of instruments and surgical tools can be introduced into the abdominal cavity to engage and/or treat tissue in a number of ways to achieve a diagnostic or therapeutic effect.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical clip (alternately referred to as a "ligation clip") therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to manipulate and engage surgical instruments via an electronic interface communicatively coupled to a robotic manipulator. A user need not even be in the operating room with the patient during robotic surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical systems and, more particularly, to surgical clip appliers with improved jaws that facilitate parallel closure of opposed jaw members.

Embodiments discussed herein describe improvements to jaws used in surgical clip appliers. The jaws include opposed jaw members that each include a linkage portion having two or more beam elements extending between living hinges at each axial end. The living hinges may allow the beam elements in each linkage portion to move relative to one another and thereby act as a four-bar linkage system as the jaw members move between open and closed positions. As a result, the living hinges may prove advantageous in allowing the jaw members to achieve substantially parallel closure between the opposing planar inner surfaces, which reduces the amount of force required to collapse the jaw members and crimp a surgical clip.

Figure 1:
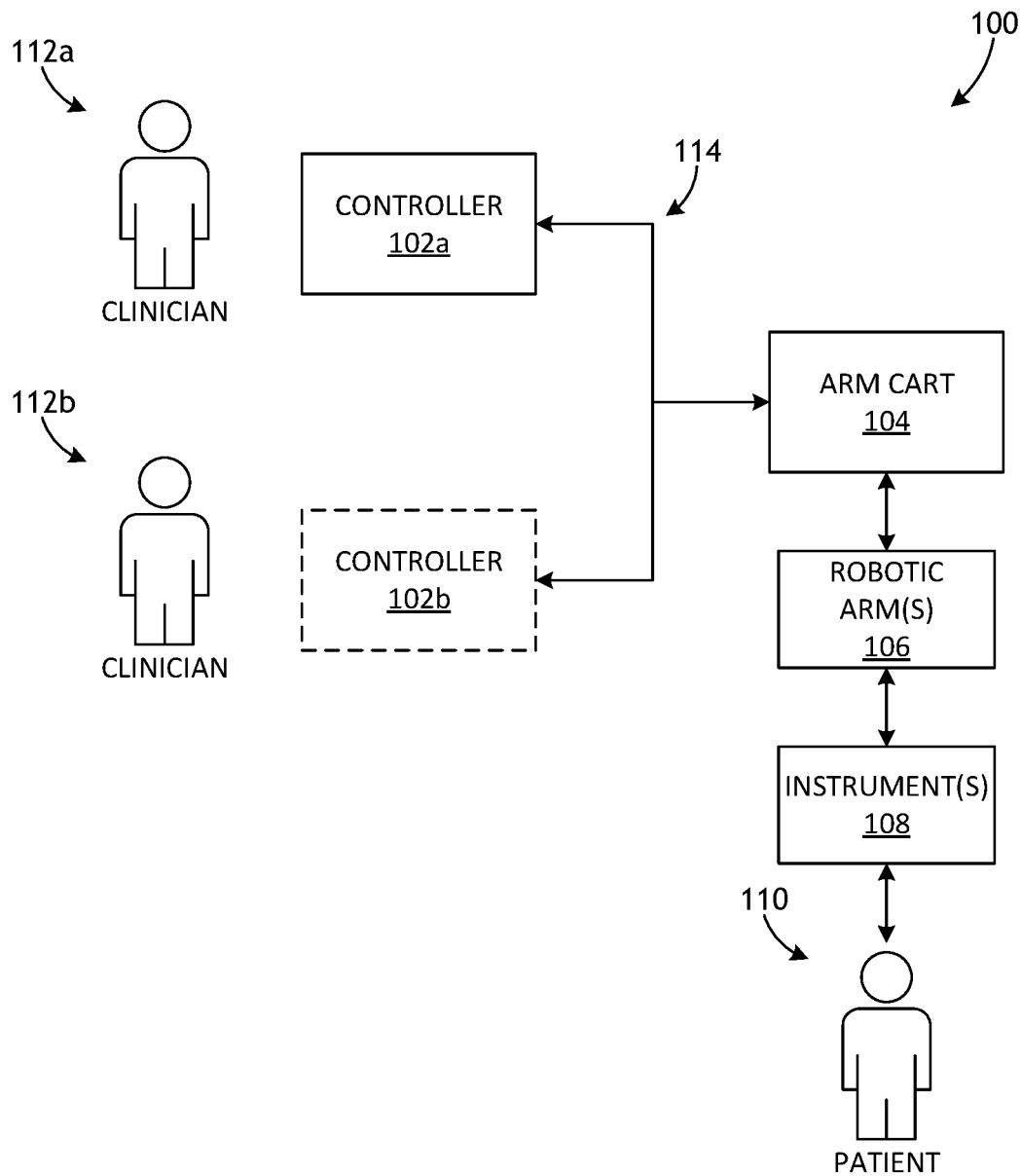
FIG. 1 is a block diagram of an example robotic surgical system that may incorporate some or all of the principles of the present disclosure.

FIGS. 1-5 illustrate the structure and operation of example robotic surgical systems and components thereof. FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 112a,b 102a,b may control different arms 106 of the arm cart 104 or, in some cases, complete control of the arm cart 104 may be passed between the clinicians 112a,b 102a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
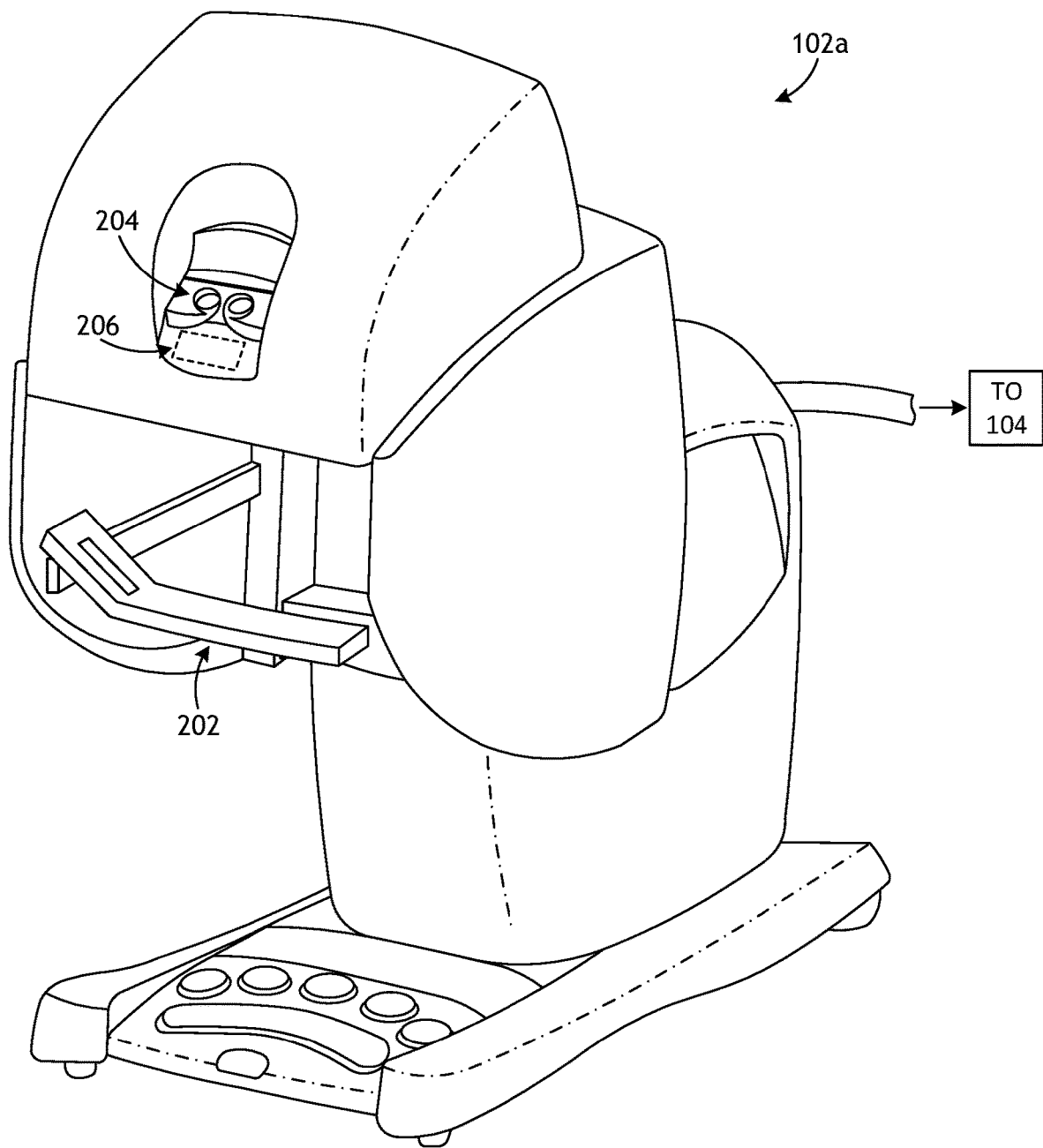
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 102a 202 generally comprise manual input devices designed to move in multiple degrees of freedom, and which often further have an actuatable handle for actuating a surgical instrument (e.g., the surgical instrument(s) 108 of FIG. 1), for example, for opening and closing opposing jaws, applying an electrical potential (current) to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
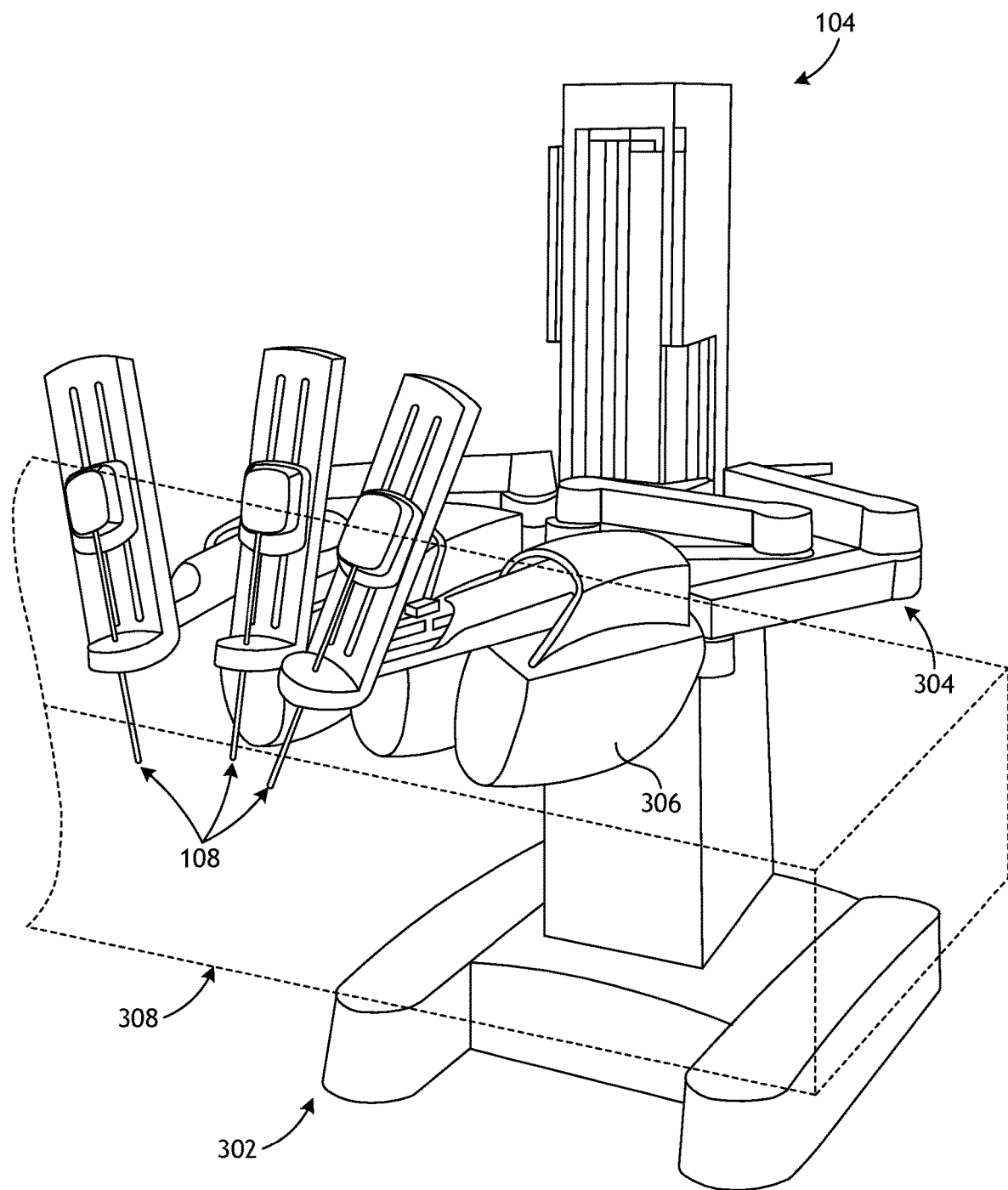
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulatable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to fit through standard operating room doors and onto standard hospital elevators. In some embodiments, the cart 104 may include a wheel system (or other transportation system) that allows the cart 104 to be positioned adjacent an operating table by a single attendant. In various embodiments, an automated reloading system including a base portion may be strategically located within a work envelope 308 of the robotic arm cart 104.

Figure 4:
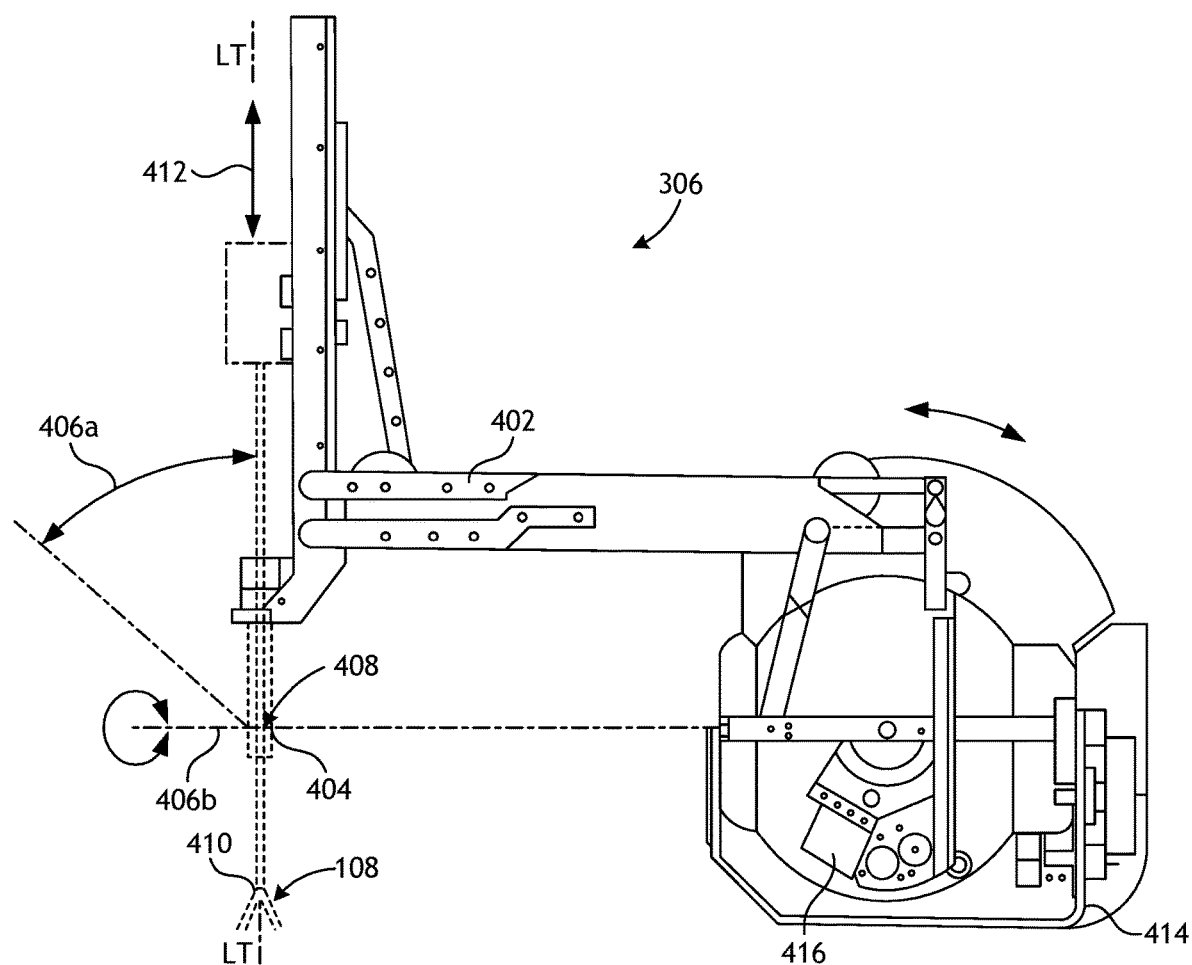
FIG. 4 is a side view schematic diagram of an example embodiment of the robotic manipulator of FIG. 3.

FIG. 4 is a side view schematic diagram of an example embodiment of the robotic manipulator 306. As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space.

The parallelogram arrangement constrains rotation to pivoting about a "pitch axis" that extends an axis through the point 404, as indicated by a pitch arrow 406a. The links supporting the parallelogram linkage 402 are pivotally mounted to set-up joints 304 (FIG. 3) so that the surgical instrument 108 further rotates about a second axis 406b, referred to as the "yaw axis." The pitch axis and the yaw axis 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the robotic manipulator 306 (arrow 412), the remote center 408 remains fixed relative to a base 414 of the robotic manipulator 306. Hence, the entire robotic manipulator 306 is generally moved to re-position the remote center 408.

The linkage 402 of the robotic manipulator 306 is driven by a series of motors 416. These motors 416 actively move the linkage 402 in response to commands from a processor of a control system. The motors 416 may also be employed to manipulate the surgical instrument 108.

Figure 5:
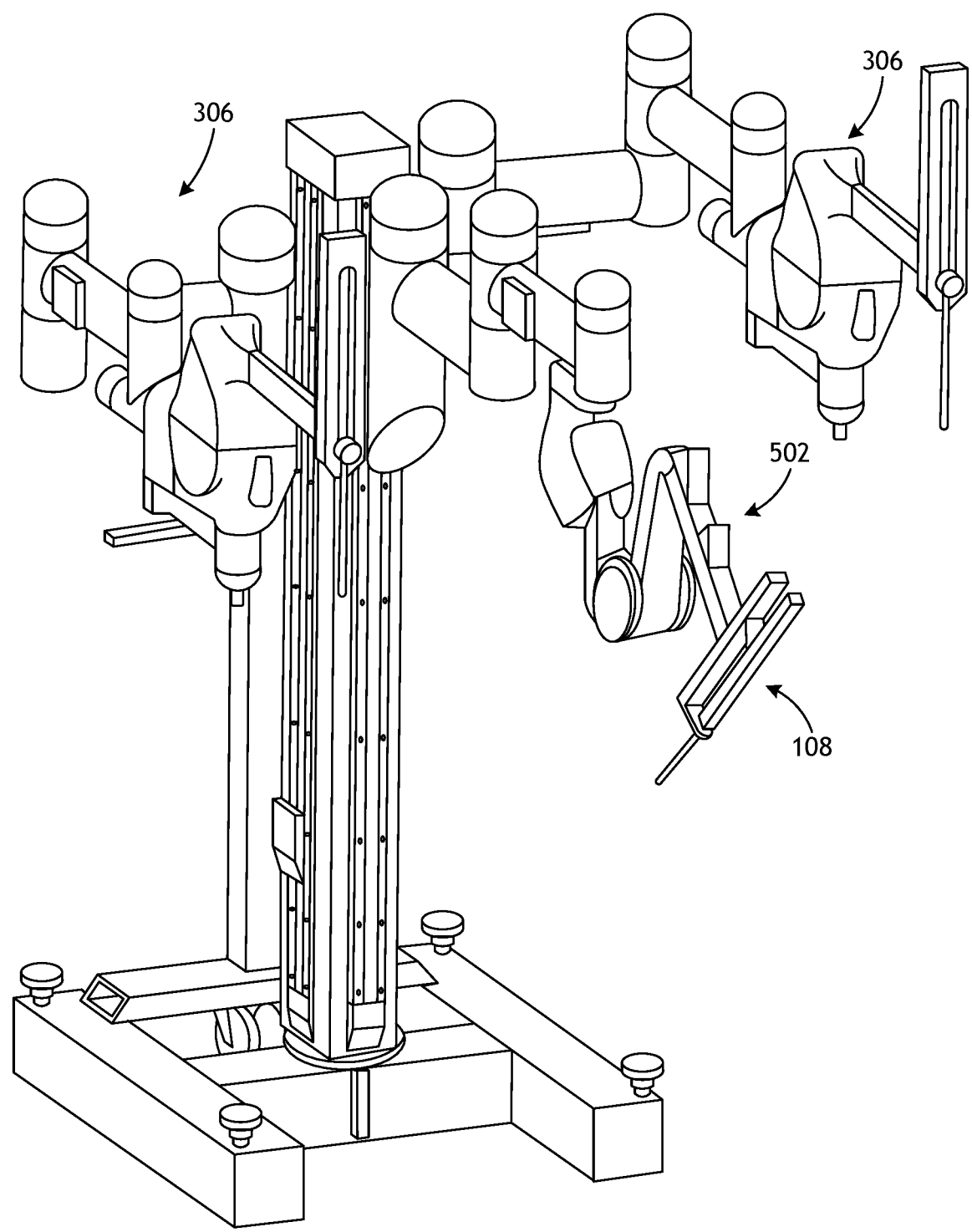
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system is primarily described herein with reference to communication between the surgical instrument 108 and the master controller 102a (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
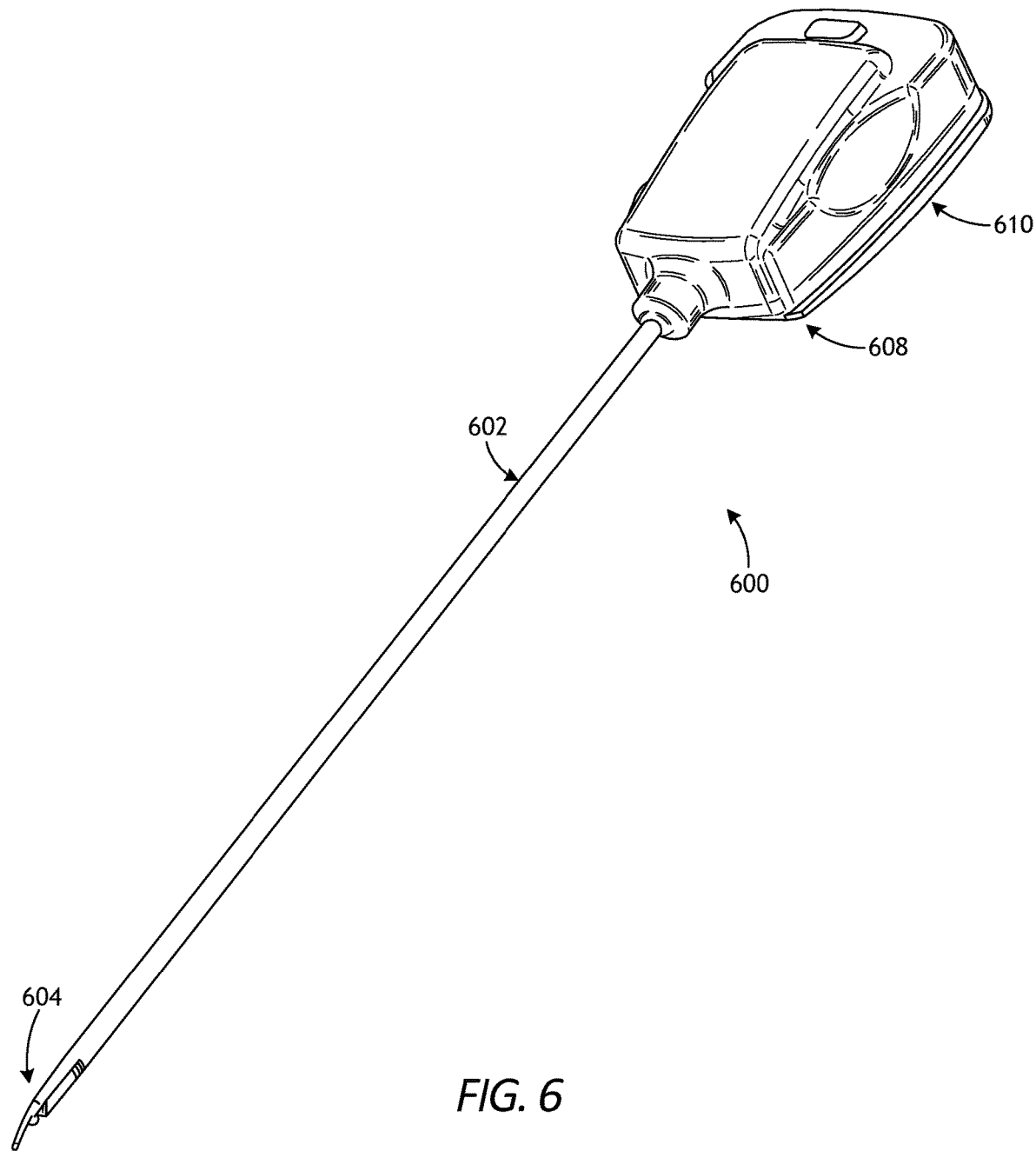
FIG. 6 is an isometric front view of an example surgical tool that may incorporate some or all of the principles of the present disclosure.

FIG. 6 is an isometric view of an example surgical tool 600 that may incorporate some or all of the principles of the present disclosure. The surgical tool 600 may be the same as or similar to the surgical instrument(s) 108 of FIGS. 1 and 3-5 and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100. The details and operation of the surgical tool 600 may be similar in some respects to the surgical tools described in U.S. Patent Pub. 2016/0287252, entitled "Clip Applier Adapted for Use with a Surgical Robot," the contents of which are hereby incorporated by reference in their entirety.

While the surgical tool 600 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 600 can include an elongate shaft 602, an end effector 604 coupled to the distal end of the shaft 602, and a drive housing 608 coupled to the proximal end of the shaft 602. In the illustrated embodiment, the end effector 604 comprises a clip applier. In applications where the surgical tool 600 is used in conjunction with a robotic surgical system (e.g., the robotic surgical system 100 of FIG. 1), the drive housing 608 can include coupling features that releasably couple the surgical tool 600 to the robotic surgical system. In such applications, the surgical tool 600 may be operably coupled to the manipulator of the robotic surgical system at a tool mounting portion 610.

The terms "proximal" and "distal" are defined herein relative to a robotic surgical system having an interface configured to mechanically and electrically couple the surgical tool 600 (e.g., the drive housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The tool mounting portion 610 may releasably attach (couple) the drive housing 608 to a tool driver in a variety of ways, such as by clamping thereto, clipping thereto, or slidably mating therewith. In some embodiments, the tool mounting portion 610 may include an array of electrical connecting pins, which may be coupled to an electrical connection on the mounting surface of the tool driver. While the tool mounting portion 610 is described herein with reference to mechanical, electrical, and magnetic coupling elements, it should be understood that a wide variety of telemetry modalities might be used, including infrared, inductive coupling, or the like.

Figure 7:
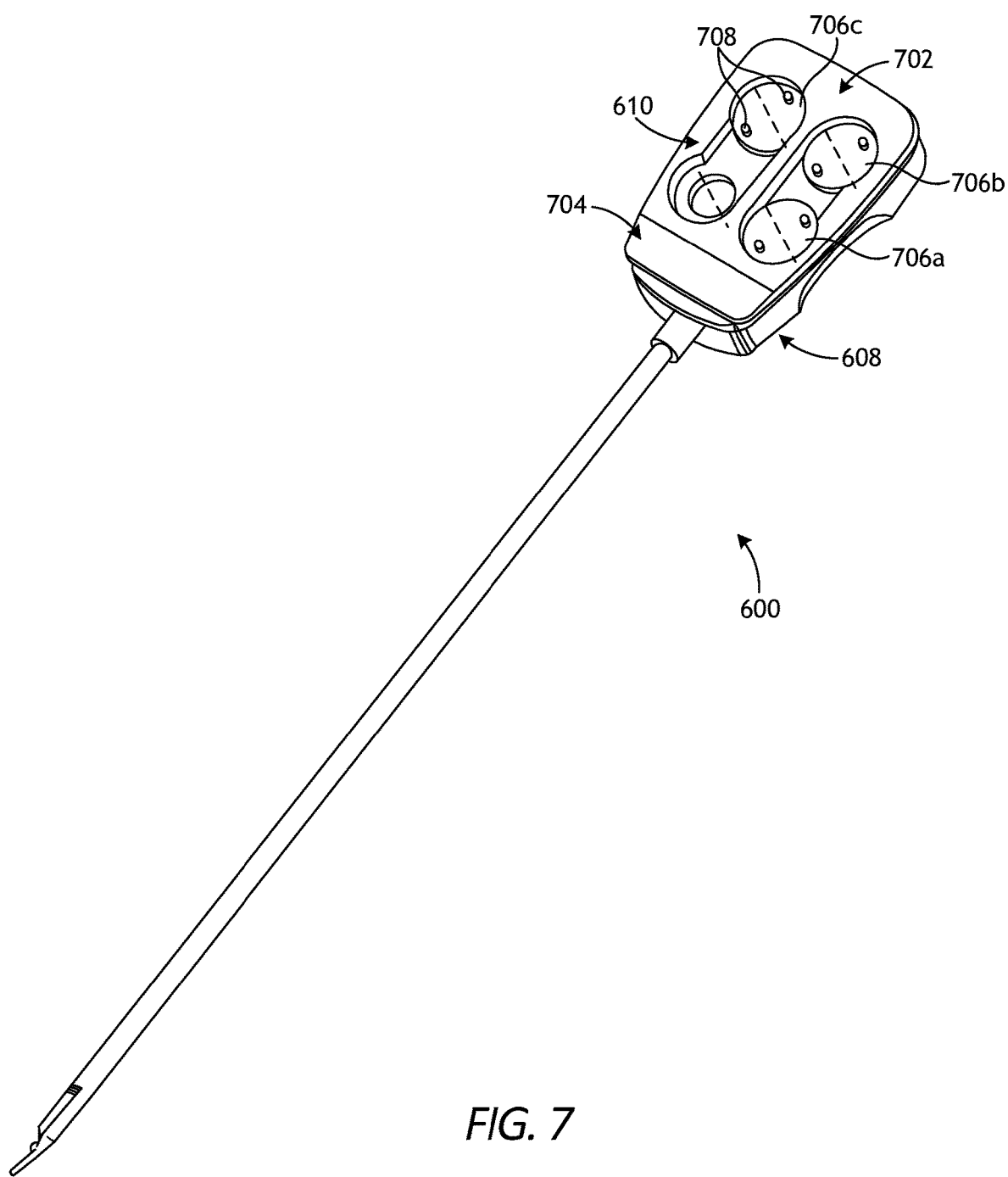
FIG. 7 is an isometric rear view of the surgical tool of FIG. 6.

FIG. 7 is an isometric rear view of the surgical tool 600. The surgical tool 600 further includes an interface 702 that mechanically and electrically couples the tool mounting portion 610 to the manipulator of a robotic surgical system. In various embodiments, the tool mounting portion 610 includes a tool mounting plate 704 that operably supports a plurality of drive inputs, shown as a first drive input 706a, a second drive input 706b, and a third drive input 706c. While only three drive inputs 706a-c are shown in FIG. 7, more or less than three may be utilized, without departing from the scope of the disclosure. In at least one embodiment, for example, six or more drive inputs may be included in the drive housing 608.

In the illustrated embodiment, the drive inputs 706a-c each comprise a rotatable disc configured to align with and couple to a corresponding input actuator (not shown) of a given tool driver. Moreover, each drive input 706a-c provides or defines one or more surface features 708 configured to align with mating surface features provided on the corresponding input actuator. The surface features 708 can include, for example, various protrusions and/or indentations that facilitate a mating engagement. In some embodiments, some or all of the drive inputs 706a-c may include one surface feature 708 that is positioned closer to an axis of rotation of the associated drive input 706a-c than the other surface feature(s) 708. This may help to ensure positive angular alignment of each drive input 706a-c.

Figure 8:
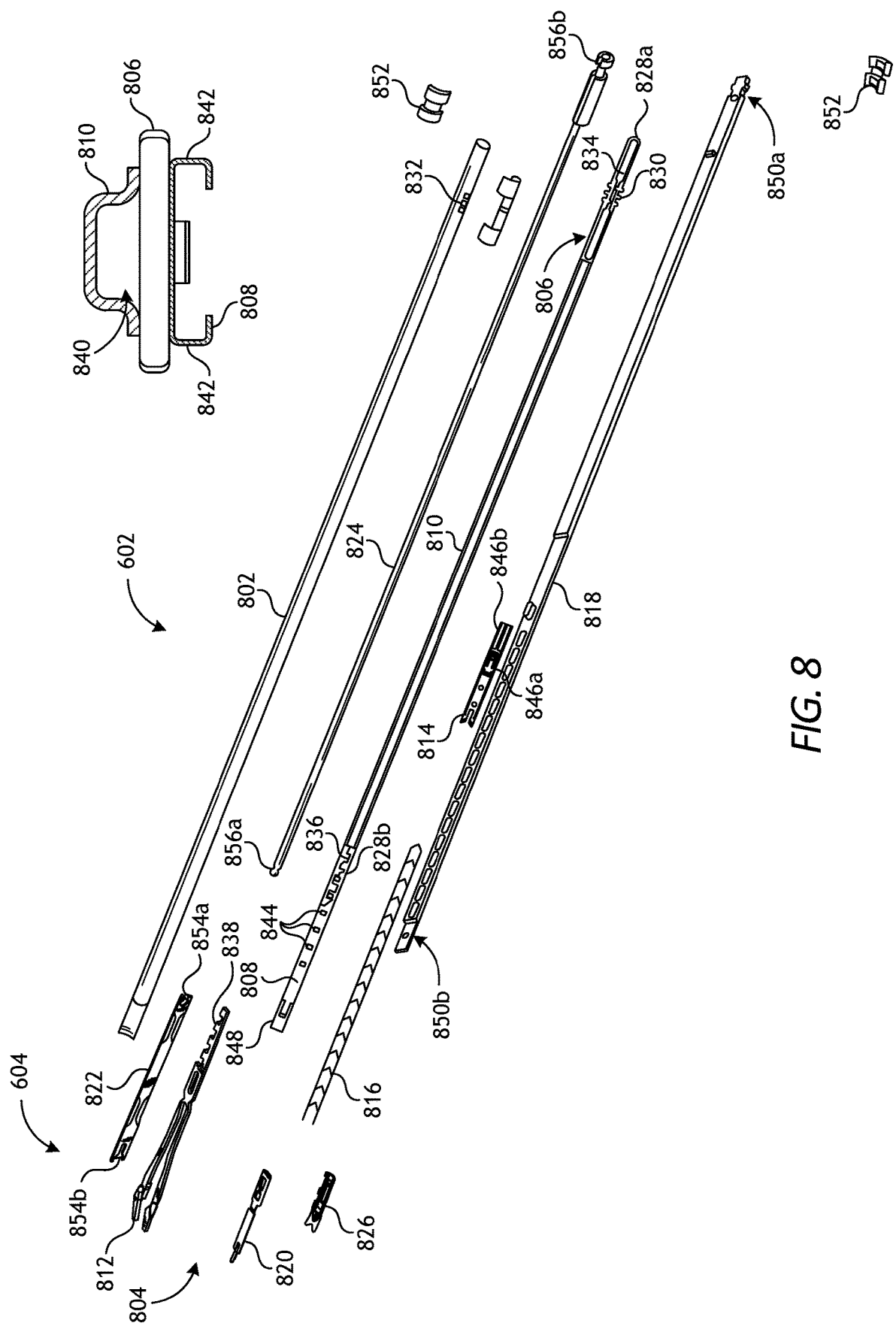
FIG. 8 is an exploded view of the elongate shaft and the end effector of the surgical tool of FIG. 6.

FIG. 8 is an exploded view of one example of the elongate shaft 602 and the end effector 604 of the surgical tool 600 of FIGS. 6 and 7, according to one or more embodiments. As illustrated, the shaft 602 includes an outer tube 802 that houses the various components of the shaft 602, which can include a jaw retaining assembly 804. The jaw retaining assembly 804 includes a jaw retainer shaft 806 with a clip track 808 and a push rod channel 810 formed thereon. The end effector 604 includes opposing jaws 812 that are configured to mate to a distal end of the clip track 808.

The shaft 602 can also include a clip advancing assembly, which, in one example embodiment, can include a feeder shoe 814 that is adapted to be slidably disposed within the clip track 808. The feeder shoe 814 may be configured to advance a series of clips 816 positioned within the clip track 808, and a feedbar 818 may be adapted to drive the feeder shoe 814 through the clip track 808. An advancer assembly 820 is adapted to mate to a distal end of the feedbar 818 for advancing a distal-most clip into the jaws 812.

The shaft 602 can further include a clip forming or camming assembly operable to collapse the jaws 812 and thereby crimp (crush) a surgical clip positioned between the jaws 812. In one example embodiment, the camming assembly includes a cam 822 that is adapted to slidably mate to the jaws 812, and a push rod 824 that can couple to the cam 822 to move the cam 822 relative to the jaws 812. The shaft assembly can also include a tissue stop 826 that can mate to a distal end of the clip track 808 for facilitating positioning of the jaws 812 relative to a surgical site.

The jaw retainer shaft 806 comprises an elongate, substantially planar structure having a proximal end 828a that mates to the outer tube 802, and a distal end 828b that is adapted to mate to the jaws 812. While a variety of techniques can be used to mate the proximal end 828a of the jaw retainer shaft 806 to the outer tube 802, in the illustrated embodiment the proximal end 828a includes teeth 830 formed on opposed sides thereof that are adapted to be received within corresponding holes or openings 832 formed in the outer tube 802. A cut-out 834 may be defined in the jaw retainer shaft 806 to allow the opposed sides of the proximal end 828a to deflect or to form a spring. In particular, the cut-out 834 allows the opposed sides of the proximal end 828a of the jaw retainer shaft 806 to be compressed toward one another when the jaw retainer shaft 806 is inserted into the outer tube 802. Once the teeth 830 align with the corresponding openings 832 in the outer tube 802, the proximal end 828a of the jaw retainer shaft 806 will return to its original, uncompressed configuration thereby causing the teeth 830 to extend into the corresponding openings 832 to engage the outer tube 802.

A variety of techniques can also be used to mate the distal end 828b of the jaw retainer shaft 806 to the jaws 812. In the illustrated embodiment, for example, the distal end 828b of the jaw retainer shaft 806 includes several cut-outs or teeth 836 formed therein for mating with corresponding protrusions or teeth 838 formed on the jaws 812. The teeth 836 allow a proximal portion of the jaws 812 to be substantially co-planar with the jaw retainer shaft 806. Other techniques, however, can be used to mate the jaws 812 to the jaw retaining shaft 806; e.g., a dovetail connection, a male-female connection, etc. Alternatively, the jaws 812 may be integrally formed with the jaw retainer shaft 806.

The push rod channel 810 formed on the jaw retainer shaft 806 may be configured to slidably receive the push rod 824, which is used to advance the cam 822 over the jaws 812. The push rod channel 810 can be formed using a variety of techniques, and it can have any shape and size depending on the shape and size of the push rod 824. As shown in the inset graphic of FIG. 8, the push rod channel 810 is fixedly attached (e.g., by welding) to a superior surface of the retainer shaft 806, and it has a substantially rectangular shape that defines a pathway 840 extending therethrough. The push rod channel 810 can also extend along all or only a portion of the jaw retainer shaft 806. A person skilled in the art, however, will appreciate that the jaw retaining assembly 804 does not need to include the push rod channel 810 for facilitating movement of the push rod 824 within the elongate shaft 602.

The clip track 808 extends distally beyond the distal end 828b of the jaw retainer shaft 806 to allow a distal end of the clip track 808 to be substantially aligned with the jaws 812. As shown in the inset graphic of FIG. 8, the clip track 808 may be mated to an inferior surface of the jaw retainer shaft 806. In some embodiments, the clip track 808 may be configured to seat at least one, and preferably a series, of surgical clips therein. To accomplish this, the clip track 808 can include opposed side rails 842 that are adapted to seat opposed legs of one or more clips therein, such that the legs of the clips are axially aligned with one another. In an exemplary embodiment, the clip track 808 can be configured to seat about twenty surgical clips that may be pre-disposed within the clip track 808 during manufacturing. A person skilled in the art will appreciate, however, that the shape, size, and configuration of the clip track 808 can vary depending on the shape, size, number and configuration of surgical clips, or other closure devices such as staples, adapted to be received therein. Moreover, a variety of other techniques can be used, instead of a clip track 808, to retain a clip supply within the elongate shaft 602.

The clip track 808 can also include several openings 844 formed therein for receiving an upper or "superior" tang 846a formed on the feeder shoe 814 adapted to be disposed within the clip track 808. The number of openings 844 in the clip track 808 may correspond to at least the number of surgical clips 816 included in the assembly and applied during use. The openings 844 are preferably spaced equidistant from one another to ensure that the superior tang 846a engages an opening 844 each time the feeder shoe 814 is advanced. In some embodiments, however, the openings 844 may be omitted and the clip track 808 may alternatively include detents or other features that allow the clip track 808 to engage the feeder shoe 814 and prevent distal movement, yet allow proximal movement, of the feeder shoe 814.

The clip track 808 can also include a stop tang 848 formed thereon that is effective to be engaged by a corresponding stop tang formed on the feeder shoe 814 to prevent movement of the feeder shoe 814 beyond a distal-most position. The stop tang 848 can have a variety of configurations, but in one exemplary embodiment, it is in the form of two adjacent tabs that extend toward one another to enclose a portion of the clip track 808, thus allowing surgical clips to pass therethrough.

To facilitate proximal movement of the feeder shoe 814 within the clip track 808, the feeder shoe 814 can also include a lower or "inferior" tang 846b formed on the inferior (underside) surface thereof for allowing the feeder shoe 814 to be engaged by the feedbar 818 as the feedbar 818 is moved distally. The inferior tang 846b is similar to the superior tang 846a in that it can be angled proximally. In use, each time the feedbar 818 is moved distally, a detent formed in the feedbar 818 engages the inferior tang 846b and moves the feeder shoe 814 distally a predetermined distance within the clip track 808. The feedbar 818 can then be moved proximally to return to its initial position, and the angle of the inferior tang 846b allows the inferior tang 846b to slide into the next detent formed in the feedbar 818. As will be appreciated, a variety of other features rather than tangs, openings, and/or detents can be used to control movement of the feeder shoe 814 within the clip track 808.

As mentioned above, the feeder shoe 814 can also include a stop tang formed thereon that is adapted to stop movement of the feeder shoe 814 when the feeder shoe 814 is in the distal-most position and there are no surgical clips remaining in the assembly. While the stop can have a variety of configurations, in at least one embodiment the stop may comprise a third tang formed on the feeder shoe 814 and extending in an inferior direction for engaging the stop tang 848 formed on the clip track 808. The third tang may be positioned such that it will engage the stop tang 848 when the feeder shoe 814 is in a distal-most position, thereby preventing movement of the feeder shoe 814 and the feedbar 818 when the clip supply is depleted.

The feedbar 818 has a generally elongate shape with proximal and distal ends 850a and 850b, respectively. The proximal end 850a is adapted to mate to a feedbar coupler 852 (two halves shown). The feedbar coupler 852 can mate to a variety of feed links that, upon actuation, are effective to slidably move the feedbar 818 in a distal direction within the elongate shaft 602, and thereby advance a clip into the jaws 812.

The distal portion of the jaws 812 include first and second opposed jaw members that are movable relative to one another and are configured to receive a surgical clip from the series of clips 816 therebetween. In at least one embodiment, the jaw members are biased to an open position, and a force is required to move the jaw members toward one another to crimp the clips. The jaw members can each include a groove formed on opposed inner surfaces thereof for receiving the legs of a surgical clip in alignment with the jaw members. The jaw members can also each include a cam track formed therein for allowing the cam 822 to engage the jaw members and move the jaw members toward one another. In at least one embodiment, the cam track is formed on a superior surface of the jaw members, but could alternatively be formed on the lateral sides of each jaw member.

The cam 822 can have a variety of configurations, but in the illustrated embodiment it includes a proximal end 854a that is adapted to mate to a distal end 856a of the push rod 824, and a distal end 854b adapted to engage and actuate the jaws 812. A variety of techniques can be used to mate the cam 822 to the push rod 824. In the illustrated embodiment, the proximal end 854a 851b of the cam 822 provides a female or keyed cut-out formed therein that is adapted to receive a male or key member formed at the distal end 856a of the push rod 824. Those skilled in the art will appreciate that the cam 822 and the push rod 824 can be coupled in various alternative ways, without departing from the scope of the disclosure, and may optionally be integrally formed with one another. The proximal end 856b of the push rod 824 can be adapted to mate to a closure link assembly, for moving the push rod 824 and the cam 822 relative to the jaws 812.

The distal end 854b of the cam 822 includes a camming channel or tapering recess (not visible) formed therein for slidably receiving corresponding cam tracks provided by the jaw members. In operation, the cam 822 can be advanced from a proximal position, in which the jaw members are spaced apart from one another, to a distal position, where the jaw members are collapsed to a closed position. As the cam 822 is advanced over the jaw members, the tapering recess at the distal end 854b serves to push the jaw members toward one another, thereby crimping a surgical clip disposed therebetween.

Figure 9:
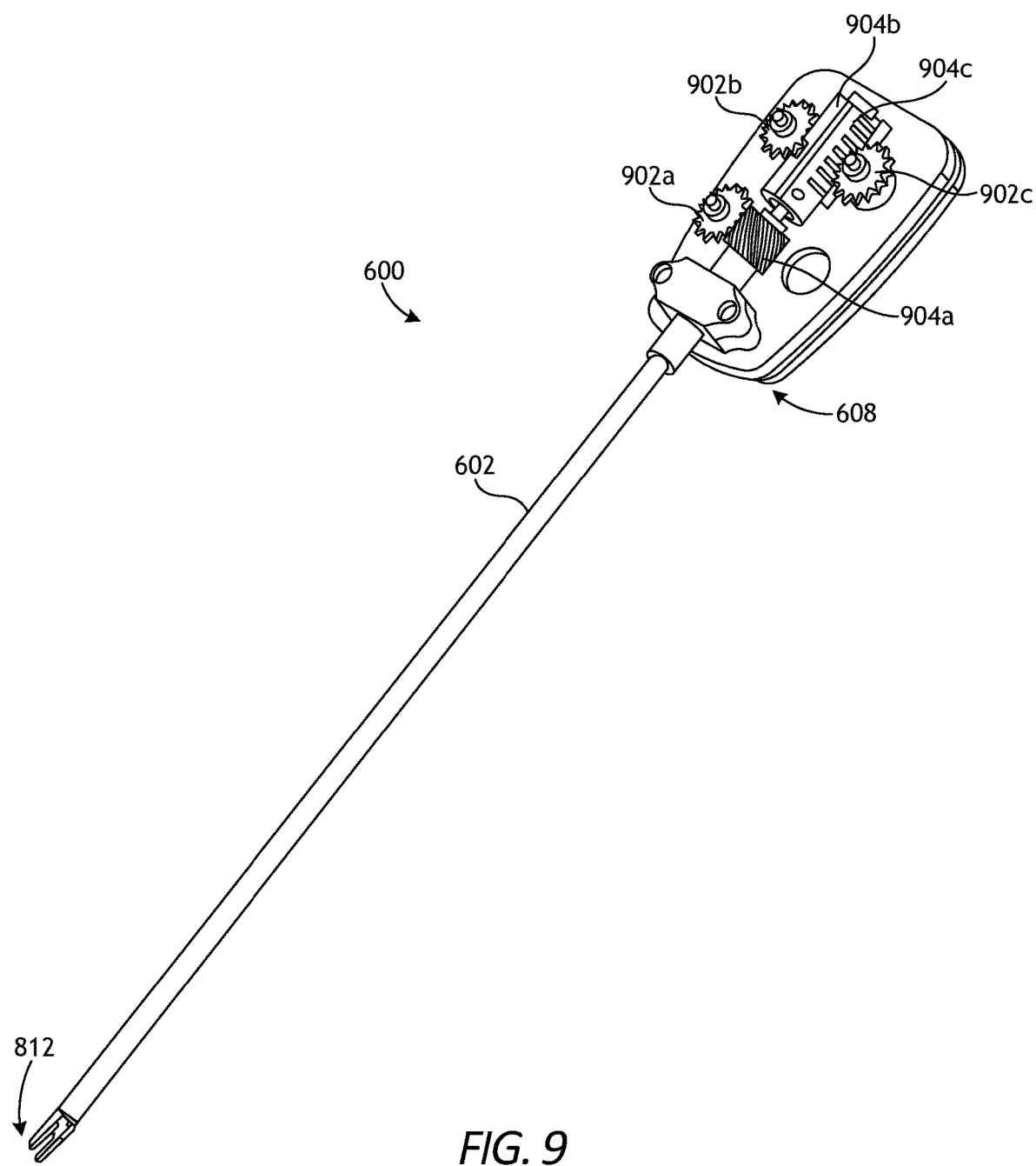
FIG. 9 is an exposed isometric view of the surgical tool of FIG. 6.

FIG. 9 is an exposed isometric view of the surgical tool 600 of FIG. 6, according to one or more embodiments. The shroud or covering of the drive housing 608 has been removed to reveal the internal component parts. As illustrated, the surgical tool 600 may include a first drive gear 902a, a second drive gear 902b, and a third drive gear 902c. The first drive gear 902a may be operatively coupled to the first drive input 706a (FIG. 7) such that actuation of the first drive input 706a correspondingly rotates the first drive gear 902a. Similarly, the second and third drive gears 902b,c may be operatively coupled to the second and third drive inputs 706b,c (FIG. 7), respectively, such that actuation of the second and third drive inputs 706b,c correspondingly rotates the second and third drive gears 902b,c, respectively.

The first drive gear 902a may be configured to intermesh with a first driven gear 904a, which is operatively coupled to the shaft 602. In the illustrated embodiment, the first drive and driven gears 902a, 904a are in the form of mating spiral worm gears. In operation, rotation of the first drive gear 902a about a first axis correspondingly rotates the first driven gear 904a about a second axis orthogonal to the first axis to control rotation of the shaft 602 in clockwise (CW) and counter-clockwise (CCW) directions based on the rotational direction of the first drive gear 902a.

The second drive gear 902b may be configured to intermesh with a second driven gear 904b (only partially visible in FIG. 9), and the third drive gear 902c may be configured to intermesh with a third driven gear 904c. In the illustrated embodiment, the second and third drive and driven gears 902b,c, 904b,c are in the form of corresponding rack and pinion interfaces, where the driven gears 904b,c comprise the rack and the drive gears 902b,c comprise the pinion. Independent rotation of the second and third drive gears 902b,c will cause the second and third driven gears 904b,c, respectively, to translate linearly relative to (independent of) one another.

In at least one embodiment, actuation (rotation) of the third drive gear 902c will result in a surgical clip being fed into the jaws 812. More particularly, the third driven gear 904c may be operatively coupled to the feedbar 818 (FIG. 8) and, upon rotation of the third drive gear 902c in a first angular direction (e.g., CCW rotation), the third driven gear 904c will advance distally and correspondingly advance the feedbar 818 a sufficient distance to fully advance a surgical clip into the jaws 812. The linear travel distance of the third driven gear 904c may vary based upon several factors, such as clip leg length and jaw length. Moreover, rotation of the third drive gear 902c may be precisely controlled by an electrical and software interface to deliver the exact linear travel to the third driven gear 904c necessary to feed a clip into the jaws 812.

Upon delivery of a clip into the jaws 812, or after a predetermined amount of rotation of the third drive gear 902c, rotation of the third drive gear 902c is reversed in a second angular direction to move the third driven gear 904c linearly in a proximal direction, which correspondingly moves the feedbar 818 proximally. This process may be repeated several times to accommodate a predetermined number of clips residing in the shaft 602. In some embodiments, the software interface may be programmed to count down the number of clips fed into the jaws 812 and display the same to the user and may further prevent the user from attempting to feed another clip once the shaft 602 is empty. It is contemplated that the software interface may alert the user when the shaft 602 contains a predetermined amount of clips.

In at least one embodiment, actuation of the second drive gear 902b will cause the jaws 812 to close or collapse to crimp a surgical clip. More particularly, the second driven gear 904b may be coupled to the proximal end 856b (FIG. 8) of the push rod 824 (FIG. 8) and, upon actuation of the second drive gear 902b in a first angular direction (e.g., CW rotation), the second driven gear 904b will be advanced linearly in a distal direction. Such distal linear motion of the second driven gear 904b correspondingly drives the push rod 824 in a distal linear direction, which drives the cam 822 over the jaws 812 to collapse the jaw members and crimp a surgical clip positioned in the jaws 812. Rotation of the second drive gear 902b may be precisely controlled to impart a sufficient number of rotations to advance the second driven gear 904b a predetermined linear distance to fully crimp the surgical clip. Alternatively, the second drive gear 902b may be rotated slowly and stopped to permit partial formation of a surgical clip about an anatomic structure, which enables movement of the clip in a less than fully formed state about an anatomic structure.

Once a surgical clip is successfully deployed, rotation of the second drive gear 902b is reversed in a second angular direction to move the second driven gear 904b in a proximal direction, which correspondingly moves the push rod 824 and the cam 822 proximally and permits the jaws 812 to open once again. It is contemplated herein that opening and closing of the jaws 812 may be performed independently of clip feeding, thus allowing a user to utilize the jaws 812 as a dissector, if desired.

It should be noted that the processes of delivering a surgical clip into the jaws 812 and collapsing the jaws 812 to crimp the surgical clip are not limited to the actuation mechanisms and structures described herein. In alternative embodiments, for example, the second and third driven gears 904b,c may instead comprise capstan pulleys configured to route and translate drive cables within the shaft 602. In such embodiments, the drive cables may be operatively coupled to one or more lead screws or other types of rotating members positioned within the shaft 602 near the distal end and capable of advancing the feedbar 818 to deliver a surgical clip into the jaws 812 and advancing the cam 822 to collapse the jaws 812 and crimp the surgical clip. Those skilled in the art will readily appreciate that many different mechanisms and structures may be implemented into the surgical tool 600 of FIG. 6 to carry out the above-described processes, without departing from the scope of the disclosure.

Figure 10:
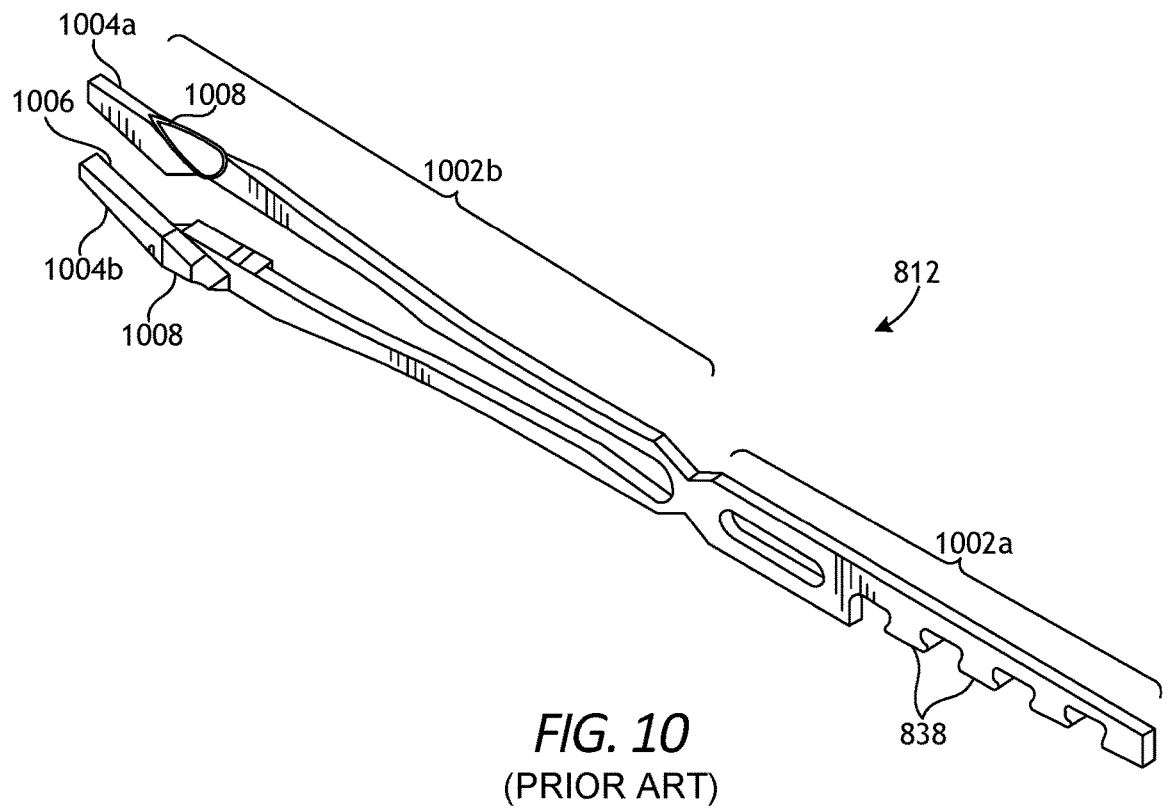
FIG. 10 is an enlarged, isometric view of one example of the jaws of FIG. 8.

FIG. 10 is an enlarged, isometric view of one example of the jaws 812 of FIG. 8. As illustrated, the jaws 812 include a proximal portion 1002a and a distal portion 1002b. The proximal portion 1002a provides the teeth 838 for mating with the corresponding teeth 836 (FIG. 8) formed on the jaw retainer shaft 806 (FIG. 8). As indicated above, however, the jaws 812 may be alternatively coupled to the jaw retainer shaft 806 in a variety of other ways or otherwise form an integral extension thereof.

The distal portion 1002b of the jaws 812 provides opposed first and second jaw members 1004a and 1004b movable relative to one another and adapted to receive a surgical clip (not shown) therebetween. In at least one embodiment, the jaw members 1004a,b are biased to an open position, and a force is required to move the jaw members 1004a,b toward one another (i.e., collapse the jaws 812). Each jaw member 1004a,b can include a groove 1006 (only one shown in FIG. 10) formed on opposed inner surfaces thereof for receiving the legs of a surgical clip in alignment with the jaw members 1004a,b. Each jaw member 1004a,b can also include a cam track 1008 formed thereon. The cam 822 may be configured to engage the jaw members 1004a,b at the cam tracks 1008 and thereby urge the jaw members 1004a,b to collapse toward one another. In the illustrated embodiment, the cam tracks 1008 are essentially ramped features formed on a superior (upper) surface of each jaw member 1004a,b. In other embodiments, however, the cam tracks 1008 may be formed and otherwise provided on the outer lateral sides of each jaw member 1004a,b, without departing from the scope of the disclosure.

Figure 11:
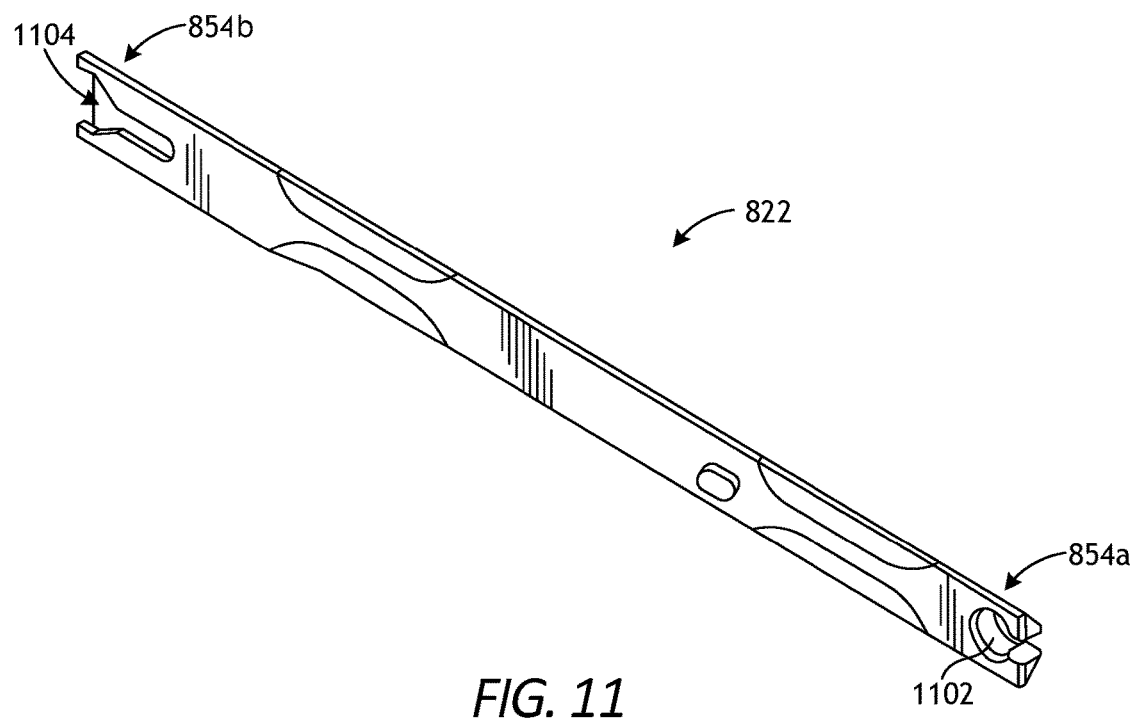
FIG. 11 is an enlarged isometric view of one example of the cam of FIG. 8.
Figure 12:
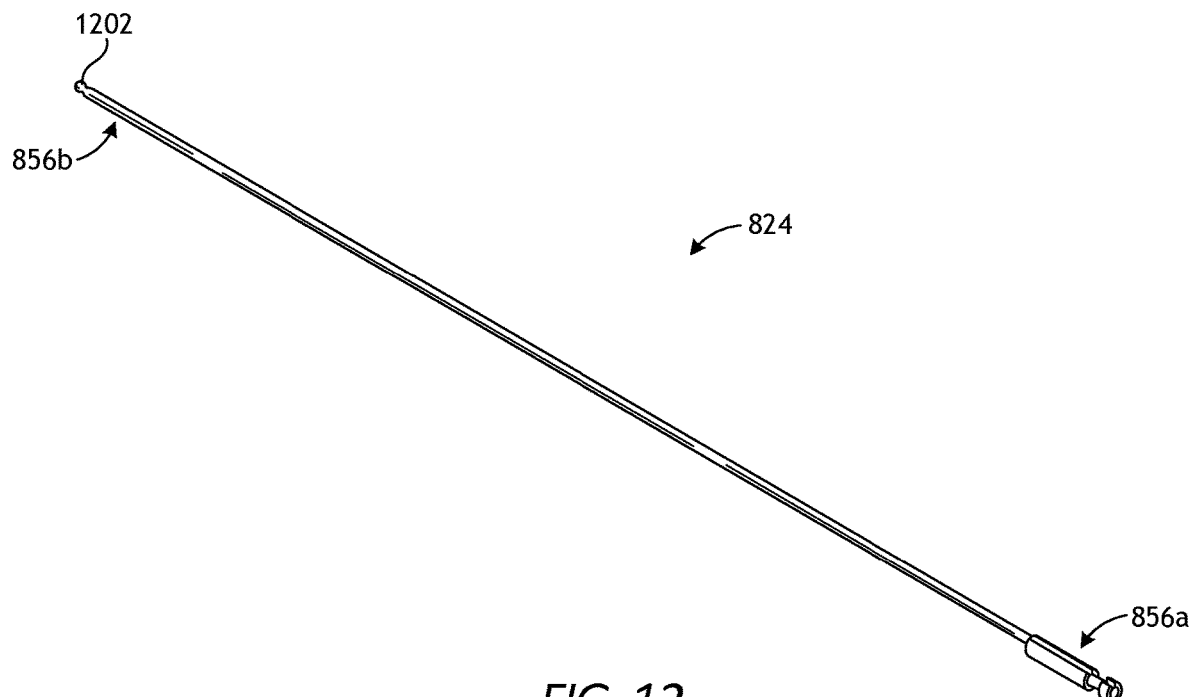
FIG. 12 is an isometric view of one example of the push rod of FIG. 8.

FIG. 11 is an enlarged isometric view of one example of the cam 822 of FIG. 8, and FIG. 12 is an isometric view of one example of the push rod 824 of FIG. 8. The cam 822 may be configured for slidably mating with and engaging the jaw members 1004a,b (FIG. 10). As mentioned above, the proximal end 854a of the cam 822 is matable with the distal end 856a of the push rod 824. As illustrated, the proximal end 854b of the cam 822 provides a female or keyed cut-out 1102 formed therein to receive a male or key member 1202 formed at the distal end 856a of the push rod 824. As will be appreciated, the cam 822 and the push rod 824 may alternatively be integrally formed with one another. The proximal end 856a of the push rod 824 can be adapted to mate to a closure link assembly for moving the push rod 824 and the cam 822 relative to the jaws 812 (FIG. 10).

Referring to FIG. 11, the distal end 854b of the cam 822 is adapted to engage and actuate the jaws 812 (FIG. 10). More specifically, in the illustrated embodiment, a camming channel or tapering recess 1104 is formed or otherwise provided at the distal end 854b of the cam 822. During actuation, the tapering recess 1104 is configured to slidably receive the cam tracks 1008 (FIG. 10) provided by the jaw members 1004a,b, and further movement of the cam 822 relative to the jaws 812 will urge the jaw members 1004a,b to collapse toward each other.

Figure 13A:
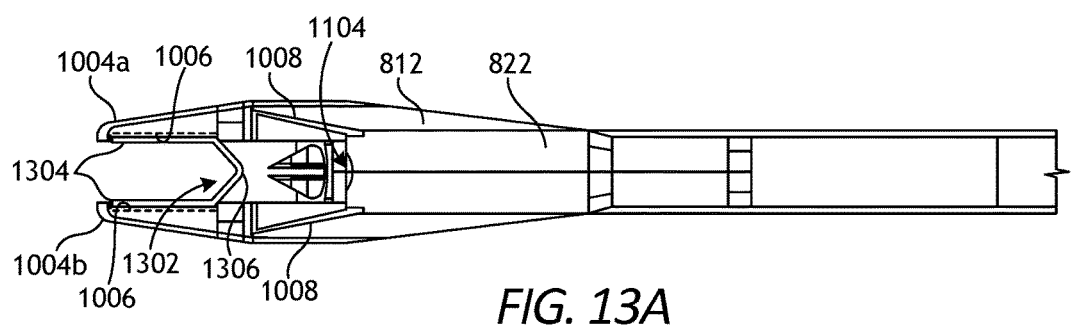
FIGS. 13A and 13B illustrate example operation of the cam and the jaws.
Figure 13B:
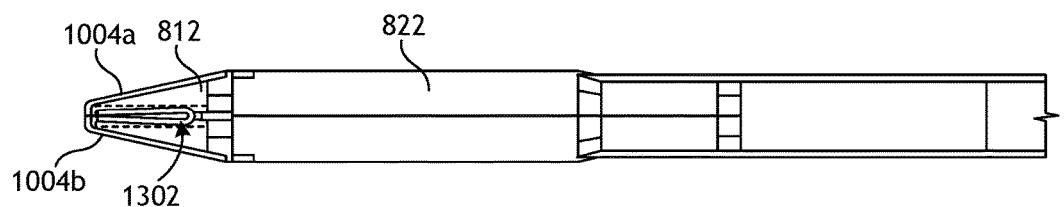

FIGS. 13A and 13B illustrate example operation of the cam 822 and the jaws 812. In FIG. 13A, a surgical clip 1302 has been previously advanced to the jaws 812. As illustrated, the legs 1304 of the surgical clip 1302 are received within the grooves 1006 defined in the opposed inner surfaces of the jaw members 1004a,b, and the apex 1306 is positioned between the jaw members 1004a,b and points proximally.

To crimp the surgical clip 1302, the cam 822 is advanced distally (i.e., to the left in FIGS. 13A and 13B) relative to the jaws 812. In FIG. 13A, the cam 822 is shown in a proximal position, where the jaw members 1004a,b are spaced apart from one another. As the cam 822 is advanced distally over the jaw members 1004a,b, the tapering recess 1104 receives and slidingly engages the angled surfaces of the cam tracks 1008, which simultaneously urges the jaw members 1004a,b to collapse toward one another and crimp the surgical clip 1302. FIG. 13B shows the crimped surgical clip 1302.

During distal movement of the cam 822, the jaw members 1004a,b act as individual cantilever beams as they are urged toward one another by the cam 822. Because the jaw members 1004a,b act as cantilever beams, the distal ends or "tips" of the jaw members 1004a,b come together first, at which point each jaw member 1004a,b is effectively converted into a fixed-pinned beam, which increases the stiffness of the system. As opposed pinned-pinned beams, the lateral force required to fully close the jaw members 1004a,b along the length of the grooves 1006 increases dramatically. In some applications, for example, 70 lbf-80 lbf of force is required to fully close the jaw members 1004a,b. Consequently, this requires more expensive and powerful actuators to move (actuate) the cam 822 and necessitates more robust materials used to make the jaws 812, the cam 822, and other intervening structural elements that facilitate jaw 812 actuation.

According to embodiments of the present disclosure, robotic clip appliers may incorporate improved jaws that eliminate distal tip-to-tip closure of its corresponding jaw members. Rather, as described herein, the improved jaws may be designed to achieve parallel (or substantially parallel) closure between the corresponding jaw members. As used herein, the term "substantially parallel" can refer to true relative parallelism between opposing members or near true relative parallelism, without departing from the scope of the disclosure. Eliminating tip-to-tip closure eliminates the need to deflect the opposed jaw members between supported ends, which may prove advantageous in eliminating the additional reaction load from the opposing jaw member and minimizing jaw length. Moreover, substantial parallel closure between opposed jaw members may prove advantageous in reducing manufacturing costs. Conventional clip applier jaws, for example, are typically manufactured of robust materials via stamping or machining processes to accommodate the large forces required to fully close the jaws. Jaws capable of facilitating parallel closure of opposed jaw members, however, may require less force to fully close the jaws, which allows the jaws to be manufactured of less expensive materials and via less expensive manufacturing processes.

Figure 14:
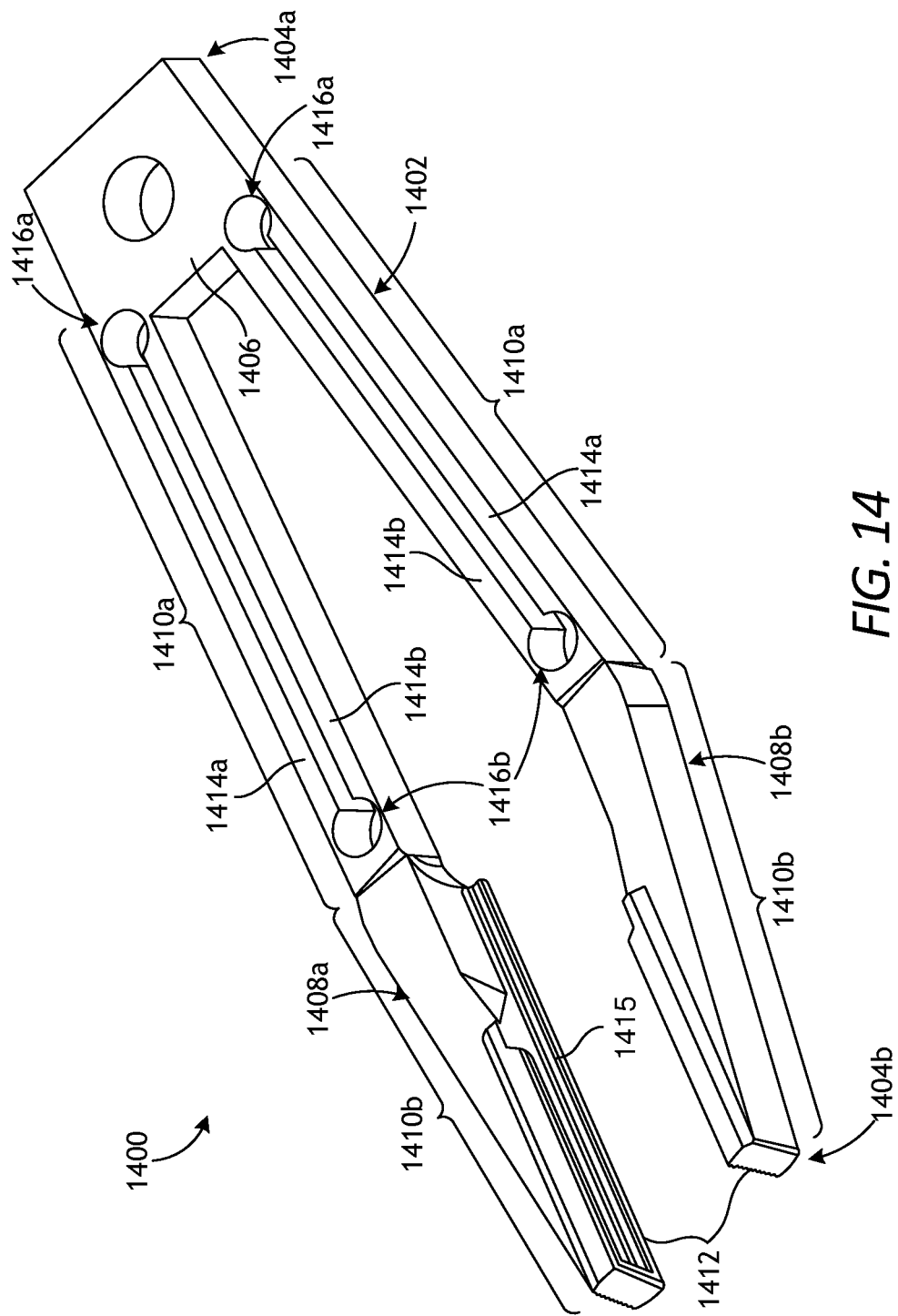
FIG. 14 is an isometric view of example jaws.

FIG. 14 is an isometric view of example jaws 1400, according to one or more embodiments of the present disclosure. The jaws 1400 may be similar in some respects to the jaws 812 of FIG. 10 and therefore may be best understood with reference thereto. Moreover, the jaws 1400 may replace the jaws 812 in any of the above-described embodiments. Accordingly, the jaws 1400 may be incorporated into the surgical tool 600 of FIG. 6 and otherwise form part of the end effector 604 (FIG. 6).

As illustrated, the jaws 1400 comprise a one-piece body 1402 having a first or proximal end 1404a and a second or distal end 1404b. A transverse member 1406 (alternately referred to as a "linkage") may be provided at the proximal end 1404a, and opposed first and second jaw members 1408a and 1408b extend distally from the transverse member 1406 and toward the distal end 1404b. The transverse member 1406 provides a structural connection between the jaw members 1408a,b that allows the jaw members 1408a,b to move relative to one another (e.g., away from and toward one another) during operation.

In some embodiments, the proximal end 1404a may be operatively coupled to the jaw retainer shaft 806 (FIG. 8) to stabilize the jaws 1400 against longitudinal movement during operation. It is contemplated herein that the proximal end 1404a of the jaws 1400 may be operatively coupled to the distal end 828b (FIG. 8) of the jaw retainer shaft 806 via a variety of coupling means. Suitable coupling means include, but are not limited to, mating opposed teeth, a dovetail connection, a male-female connection, one or more mechanical fasteners, or any combination thereof. Alternatively, the jaws 1400 may comprise an integral extension of the jaw retainer shaft 806, without departing from the scope of the disclosure. In at least one embodiment, the proximal end 1404a may be operatively coupled to the distal end 828b of the jaw retainer shaft 806 via a male-female hole and pin connection or coupling joint.

The jaw members 1408a,b are naturally biased to an open position, as shown in FIG. 14, and adapted to receive a surgical clip (not shown) therebetween. Each jaw member 1408a,b may include a linkage portion 1410a and a crimping portion 1410b. The linkage portion 1410a is coupled to and extends distally from the transverse member 1406, and the crimping portion 1410b is coupled to and extends distally from the linkage portion 1410a. Each crimping portion 1410b provides an inner surface 1412 and a groove 1415 is defined in each inner surface 1412 (only one groove visible in FIG. 14). As discussed below, the grooves 1415 may be configured to receive the opposing legs of a surgical clip in alignment with the jaw members 1408a,b.

The linkage portion 1410a of each jaw member 1408a,b includes two or more beam elements, depicted as first and second beam elements 1414a and 1414b. While only two beam elements 1414a,b are included in each linkage portion 1410a, more than two beam elements 1414a,b may be employed in each linkage portion 1410a, without departing from the scope of the disclosure. Each beam element 1414a,b extends longitudinally between a first or proximal living hinge 1416a and a second or distal living hinge 1416b. The living hinges 1416a,b are defined at the axial ends of the linkage portion 1410a and comprise reduced-mass areas of the linkage portion 1410a. While the living hinges 1416a,b are each defined by a generally circular shape, it is contemplated herein that other shapes may also be used to define the living hinges 1416a,b, such as ovular or polygonal shapes, without departing from the scope of the disclosure. Indeed, the living hinges 1416a,b (alternately referred to as "bridges") can exhibit any geometry that provides a continuous, thin, and flexible section that connects the beam elements 1414a,b.

The living hinges 1416a,b help naturally bias the jaw members 1408a,b to the open position. More importantly, however, the living hinges 1416a,b may allow the opposing beam elements 1414a,b in each linkage portion 1410a to move relative to one another, which allows the linkage portion 1410a to act as a four-bar linkage system as the jaw members 1408a,b move between open and closed positions. In contrast to the design and function of conventional jaws (e.g., the jaws 812 of FIGS. 8 and 10), the living hinges 1416a,b of the jaws 1400 allow the jaw members 1408a,b to achieve parallel closure between the opposing inner surfaces 1412. Parallel closure of the opposing inner surfaces 1412 may prove advantageous in reducing the amount of force required to collapse the jaw members 1408a,b. As used herein, the phrase "move relative to one another," "move relative to each other," or any variation thereof, refers to the motion of one body with respect to another regarded as fixed. In the present context, for example, as the jaw members 1408a,b close, the living hinges 1416a,b allow the inner second beam element 1414b in each linkage portion 1410a to longitudinally move (e.g., shift) with respect to the outer first beam element 1414a, which remains substantially fixed in the longitudinal direction.

As used herein, the phrase "parallel closure" refers to the relative parallel disposition of the opposing inner surfaces 1412 of the jaw members 1408a,b throughout their entire range of motion as the jaw members 1408a,b move between open and closed positions. Parallel closure is often used with respect to medical device end effectors and is desirable to minimize tissue damage due to non-uniform pressure or milking (squeezing out) of tissue from between opposed jaw members. Because the adjacent beam elements 1414a,b in each jaw member 1408a,b are able to move relative to one another, the inner surfaces 1412 are able to maintain a parallel or substantially parallel correlation (juxtaposition) while collapsing toward the closed position.

Figure 15A:
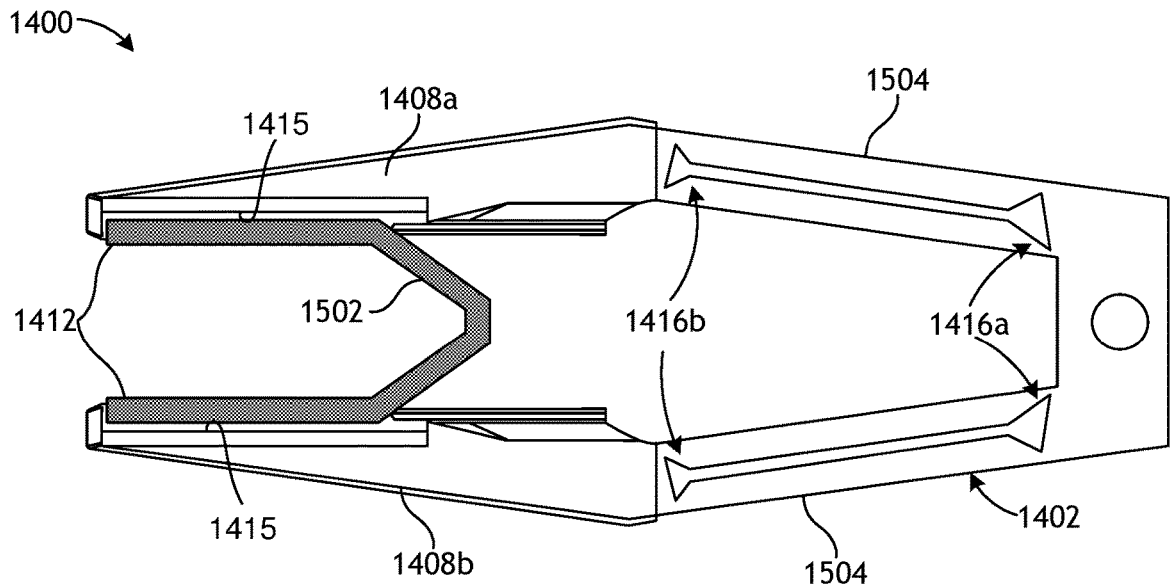
FIGS. 15A and 15B are side views of the jaws of FIG. 14 during example operation.
Figure 15B:
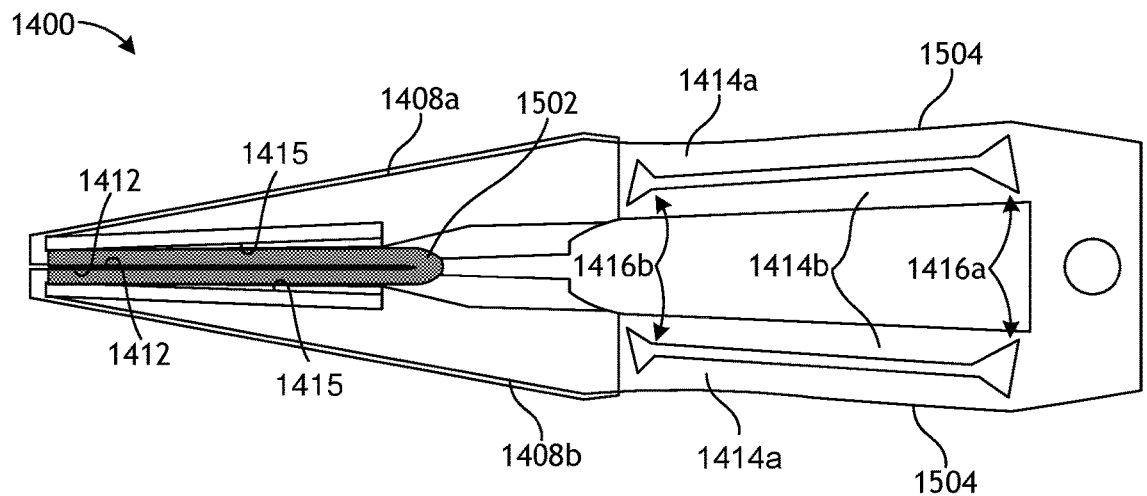

FIGS. 15A and 15B are side views of the jaws 1400 during example operation, according to one or more embodiments of the present disclosure. More specifically, FIG. 15A depicts the jaws 1400 in the open position, and FIG. 15B depicts the jaws 1400 after having been moved (actuated) to a closed position. In the illustrated embodiment, a surgical clip 1502 is depicted as being received within the groove 1415 defined in each inner surface 1412 of the jaw members 1408a,b. More specifically, opposing legs of the surgical clip 1502 are received within the groove 1415 of each inner surface 1412. Moreover, in the illustrated embodiment, the living hinges 1416a,b are defined in the body 1402 with polygonal cross-sectional shapes, as opposed to the circular cross-sectional shape employed in FIG. 14.

Each jaw member 1408a,b may include a cam track 1504 (alternately referred to as a "camming surface") formed or otherwise defined thereon and used as an engagement surface for a cam (e.g., the cam 822 of FIGS. 8 and 11) to urge the jaw members 1408a,b to collapse toward one another. In some embodiments, as illustrated, the opposing cam tracks 1504 may be provided on the outer lateral sides of each jaw member 1408a,b, such as along the outer edges of the linkage portions 1410a (FIG. 14). In such embodiments, the cam used to collapse the jaw members 1408a,b may comprise a box cam configured to extend over the outer lateral sides of each jaw member 1408a,b. In other embodiments, however, the cam tracks 1504 may be substantially similar to the cam tracks 1008 of FIGS. 8 and 13A and provided on the crimping portion 1410b (FIG. 14) and otherwise comprise ramped features formed on an internal surface of each jaw member 1408a,b, without departing from the scope of the disclosure.

To move the jaws 1400 to the closed position, a cam (e.g., the cam 822 of FIGS. 8 and 11) may be advanced distally (i.e., to the left in FIGS. 15A and 15B) relative to the jaws 1400. In other embodiments, the jaws 1400 may be designed such that the cam may be advanced proximally to move the jaws 1400 to the closed position, without departing from the scope of the disclosure. A tapering recess (e.g., the tapering recess 1104 of FIG. 4) or the like provided by the cam may receive and slidingly engage the cam tracks 1504, which simultaneously urges the jaw members 1408a,b to collapse toward one another and crimp the surgical clip 1502.

FIG. 15B shows the surgical clip 1502 crimped between the opposing jaw members 1408a,b. As the jaw members 1408a,b collapse toward each other during actuation, the living hinges 1416*a,b* defined in each jaw member 1408*a,b* allow the beam elements 1414*a,b* to move relative to one another. Moreover, relative movement of the adjacent beam elements 1414*a,b* allows the planar inner surfaces 1412 of each jaw member 1408*a,b* to approach each other in a parallel or substantially parallel trajectory (direction), and thereby provides a simultaneous and uniform crimping of the surgical clip 1502. In some embodiments, the living hinges 1416*a,b* and corresponding beam elements 1414*a,b* may be elastically deformable and, therefore, configured to return to its natural state following actuation (e.g., after each surgical clip 1502 is fired). In other embodiments, however, one or both of the living hinges 1416*a,b* and corresponding beam elements 1414*a,b* may be plastically deformable, without departing from the scope of the disclosure.

Compared to conventional clip applier jaws, the presently described jaws 1400 may prove advantageous for a variety of reasons. Conventional jaws have jaw members that act as cantilever beams as they are forced together during actuation. This results in the distal ends or tips of the jaw members touching first during actuation. Once the tips touch, the jaw members are effectively converted into continuous metal beams supported at each end instead having a free end. As a result, a great deal of additional force is required to deform the middle of the jaw members to achieve full collapse of the jaws. Testing has shown that upwards of 70-80 lbf of force is required to fully collapse the jaw members of conventional jaws to crimp the surgical clip. The required elevated force necessitates more powerful actuators and more robust materials and manufacturing methods so that the jaws may withstand such forces. Common manufacturing methods for conventional clip appliers include stamping or machined processes. This increases the cost of conventional clip appliers.

In contrast, the presently described jaws 1400 include the living hinges 1416*a,b* that essentially convert the beam elements 1414*a,b* in each jaw member 1408*a,b* into a four-bar linkage system that allows the jaw members 1408*a,b* to achieve parallel closure and uniform crimping of the surgical clip 1502. Parallel closure dramatically reduces the force required to collapse the jaw members 1408*a,b*. In some applications, for example, the required force to adequately collapse (crimp) the surgical clip 1502 would be an order of magnitude less than conventional jaws. This advantageously allows smaller actuators to be used to collapse the jaws 1400. Moreover, this allows the jaws 1400 to be made of less-expensive materials and manufactured through less-expensive manufacturing processes. In some embodiments, for example, the jaws 1400 may be made of a plastic and injection molded. In other embodiments, the jaws 1400 may be made of a metal and molded through a metal injection molding process. In yet other embodiments, the jaws 1400 may be made of a plastic or a metal and manufactured via an additive manufacturing process (e.g., 3D printing). In even further embodiments, the jaws 1400 may be made of a metallic base with plastic overmolding, without departing from the scope of the disclosure.

The novel features of the jaws 1400 may also prove advantageous in helping to minimize the length and overall size of the jaws 1400. More specifically, since less force is required to collapse the jaws 1400, less jaw length is required to help deflect a cantilever beam-type jaw member. Consequently, the length of the jaws 1400 can be reduced, which may prove advantageous in minimizing the length of a clip applier past an articulation joint or wrist, for example.

Embodiments disclosed herein include:

A. A surgical clip applier that includes a drive housing, an elongate shaft that extends from the drive housing, and an end effector arranged at a distal end of the elongate shaft, the end effector including jaws that comprise a one-piece body having opposed first and second jaw members, wherein the first jaw member provides a first inner surface and the second jaw member provides a second inner surface arranged opposite the first inner surface, and wherein the first and second inner surfaces remain substantially parallel to each other as the first and second jaw members move from an open position to a closed position to crimp a surgical clip positioned between the first and second inner surfaces.

B. A method of operating a surgical clip applier, the method including positioning the surgical clip applier adjacent a patient for operation, the surgical clip applier including a drive housing, an elongate shaft that extends from the drive housing, and an end effector arranged at a distal end of the elongate shaft and including jaws that comprise a one-piece body having opposed first and second jaw members. The method further including actuating the surgical clip applier to move the first and second jaw members from an open position to a closed position, wherein the first jaw member provides a first inner surface and the second jaw member provides a second inner surface opposite the first inner surface, maintaining the first and second inner surfaces substantially parallel to each other as the first and second jaw members move to the closed position, and crimping a surgical clip disposed between the first and second jaw members.

C. An end effector for a surgical clip applier that includes jaws that comprise a one-piece body having opposed first and second jaw members, a first inner surface defined on the first jaw member, and a second inner surface defined on the second jaw member and opposite the first inner surface, wherein the first and second inner surfaces remain substantially parallel to each other as the first and second jaw members move from an open position to a closed position.

Each of embodiments A, B, and C may have one or more of the following additional elements in any combination: Element 1: wherein each jaw member further comprises a linkage portion that includes two or more beam elements, wherein each beam element extends longitudinally between a first living hinge and a second living hinge defined in the linkage portion, and a crimping portion extending distally from the linkage portion and providing the first and second inner surfaces. Element 2: wherein the first and second living hinges are defined at axial ends of the linkage portion and comprise reduced-mass areas of the linkage portion. Element 3: wherein the two or more beam elements of each jaw member move relative to each other as the first and second jaw members move to the closed position. Element 4: further comprising a groove defined in each of the first and second inner surfaces for receiving legs of a surgical clip. Element 5: wherein each jaw member further provides a cam track engageable with a cam to move the first and second jaw members to the closed position. Element 6: wherein the cam track of each jaw member comprises a ramped feature formed on an outer lateral side of each jaw member. Element 7: wherein the cam track of each jaw member comprises a ramped feature formed on an internal surface of each jaw member.

Element 8: herein each jaw member further includes a linkage portion and a crimping portion extending distally from the linkage portion, the linkage portion including two or more beam elements and each beam element extending longitudinally between a first living hinge and a second living hinge defined by the linkage portion, the method further comprising achieving substantially parallel closure of the first and second jaw members by moving the two or more beam elements of each jaw member relative to each other as the first and second jaw members move to the closed position.

Element 9: wherein each jaw member further comprises a linkage portion that includes two or more beam elements, wherein each beam element extends longitudinally between a first living hinge and a second living hinge defined in the linkage portion, and a crimping portion extending distally from the linkage portion and providing the first and second inner surfaces. Element 10: wherein the first and second living hinges are defined at axial ends of the linkage portion and comprise reduced-mass areas of the linkage portion. Element 11: wherein the first and second living hinges exhibit a polygonal or circular cross-sectional shape. Element 12: wherein the two or more beam elements and the corresponding first and second living hinges naturally bias the first and second jaw members to the open position. Element 13: wherein the two or more beam elements of each jaw member move relative to each other as the first and second jaw members move to the closed position. Element 14: wherein the jaws are made of metal or plastic and are manufactured by molding or an additive manufacturing process. Element 15: further comprising a groove defined in each of the first and second inner surfaces for receiving legs of a surgical clip. Element 16: wherein each jaw member further provides a cam track engageable with a cam to move the first and second jaw members to the closed position. Element 17: wherein the cam track of each jaw member comprises a ramped feature formed on an outer lateral side of each jaw member.

By way of non-limiting example, exemplary combinations applicable to A, B, and C include: Element 1 with Element 2; Element 1 with Element 3; Element 5 with Element 6; Element 4 with Element 7; Element 9 with Element 10; Element 9 with Element 11; Element 9 with Element 12; Element 9 with Element 13; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical clip applier, comprising:
a drive housing;
an elongate shaft that extends from the drive housing; and
an end effector arranged at a distal end of the elongate shaft, the end effector including jaws that comprise a one-piece body having opposed first and second jaw members, wherein each jaw member provides a linkage portion including first and second beam elements extending longitudinally between a first living hinge and a second living hinge defined in the linkage portion, wherein the first jaw member provides a first inner surface and the second jaw member provides a second inner surface arranged opposite the first inner surface, wherein, as the first and second jaw members move from an open position to a closed position, the second beam element longitudinally moves with respect to the first beam element of each jaw member, and wherein the first and second inner surfaces remain parallel to each other throughout an entire range of motion as the first and second jaw members move between the open and closed positions.

2. The surgical clip applier of claim 1, wherein each jaw member further provides a crimping portion extending distally from the linkage portion and providing the first and second inner surfaces.

3. The surgical clip applier of claim 2, wherein the first and second living hinges are defined at axial ends of the linkage portion and comprise reduced-mass areas of the linkage portion.

4. The surgical clip applier of claim 1, further comprising a groove defined in each of the first and second inner surfaces for receiving legs of a surgical clip.

5. The surgical clip applier of claim 1, wherein each jaw member further provides a cam track engageable with a cam to move the first and second jaw members to the closed position.

6. The surgical clip applier of claim 5, wherein the cam track of each jaw member comprises a ramped feature formed on an outer lateral side of each jaw member.

7. The surgical clip applier of claim 5, wherein the cam track of each jaw member comprises a ramped feature formed on an internal surface of each jaw member.

8. A method of operating a surgical clip applier, comprising:

positioning the surgical clip applier adjacent a patient for operation, the surgical clip applier including:

a drive housing;

an elongate shaft that extends from the drive housing; and an end effector arranged at a distal end of the elongate shaft and including jaws that comprise a one-piece body having opposed first and second jaw members, wherein each jaw member provides a linkage portion including first and second beam elements extending longitudinally between a first living hinge and a second living hinge defined in the linkage portion;

actuating the surgical clip applier to move the first and second jaw members from an open position to a closed position, wherein the first jaw member provides a first inner surface and the second jaw member provides a second inner surface opposite the first inner surface;

achieving parallel closure of the first and second jaw members by longitudinally moving the first beam element with respect to the second beam element of each jaw member as the first and second jaw members move to the closed position;

maintaining the first and second inner surfaces parallel to each other as the first and second jaw members move to the closed position; and crimping a surgical clip disposed between the first and second jaw members.

9. An end effector for a surgical clip applier, comprising:

jaws that comprise a one-piece body having opposed first and second jaw members;

a linkage portion provided by each jaw member and including first and second beam elements, wherein each beam element extends longitudinally between a first living hinge and a second living hinge defined in the linkage portion;

a first inner surface defined on the first jaw member; and a second inner surface defined on the second jaw member and opposite the first inner surface, wherein, as the first and second jaw members move from an open position to a closed position, the second beam element longitudinally moves with respect to the first beam element of each jaw member, and wherein the first and second inner surfaces remain parallel to each other throughout an entire range of motion as the first and second jaw members move between the open and closed positions.

10. The end effector of claim 9, wherein each jaw member further provides a crimping portion extending distally from the linkage portion and providing the first and second inner surfaces.

11. The end effector of claim 10, wherein the first and second living hinges are defined at axial ends of the linkage portion and comprise reduced-mass areas of the linkage portion.

12. The end effector of claim 10, wherein the first and second living hinges exhibit a polygonal or circular cross-sectional shape.

13. The end effector of claim 10, wherein the first and second beam elements and the corresponding first and second living hinges naturally bias the first and second jaw members to the open position.

14. The end effector of claim 9, wherein the jaws are made of metal or plastic and are manufactured by molding or an additive manufacturing process.

15. The end effector of claim 9, further comprising a groove defined in each of the first and second inner surfaces for receiving legs of a surgical clip.

16. The end effector of claim 9, wherein each jaw member further provides a cam track engageable with a cam to move the first and second jaw members to the closed position.

17. The end effector of claim 16, wherein the cam track of each jaw member comprises a ramped feature formed on an outer lateral side of each jaw member.

* * * * *